United States Patent
Ignatowicz

(10) Patent No.: US 7,434,986 B2
(45) Date of Patent: Oct. 14, 2008

(54) METHOD AND APPARATUS FOR MONITORING AND DETECTING DEFECTS IN PLASTIC PACKAGE SEALING

(75) Inventor: Steven Ignatowicz, Grayslake, IL (US)

(73) Assignee: Fluke Corporation, Everett, WA (US)

(*) Notice: Subject to any disclaimer, the term of this patent is extended or adjusted under 35 U.S.C. 154(b) by 0 days.

(21) Appl. No.: 11/159,871

(22) Filed: Jun. 23, 2005

(65) Prior Publication Data
US 2005/0286606 A1    Dec. 29, 2005

Related U.S. Application Data

(60) Provisional application No. 60/582,692, filed on Jun. 24, 2004.

(51) Int. Cl.
*G01N 25/00* (2006.01)
*G01J 5/00* (2006.01)
(52) U.S. Cl. .................. 374/4; 374/121; 374/45; 340/540
(58) Field of Classification Search ............. 374/4, 374/121, 45; 340/584
See application file for complete search history.

(56) References Cited

U.S. PATENT DOCUMENTS

| 5,399,016 A | 3/1995 | Martin |
| 6,224,699 B1 | 5/2001 | Bett et al. |

FOREIGN PATENT DOCUMENTS

| JP | 08184571 | 7/1996 |
| WO | WO-97/14950 | 4/1997 |

OTHER PUBLICATIONS

Pratt, William, K., Digital Image Processing: PIKS Inside, Third Edition, "Morphological Image Processing," pp. 401-418 (2001).
International Search Report dated Nov. 8, 2005 (7 pages).
Written Opinion of the International Searching Authority dated Nov. 8, 2005 (7 pages).

*Primary Examiner*—Gail Verbitsky
*Assistant Examiner*—Mirellys Jagan
(74) *Attorney, Agent, or Firm*—Marshall, Gerstein & Borun LLP

(57) ABSTRACT

An apparatus for monitoring and detecting thermal sealing defects includes a thermal imager, a controller, and an output device. The thermal imager is mounted along a process line that transports an object having at least one recently created thermal-seal. The controller includes an input that is communicably coupled to the thermal imager for receiving thermal image data of the thermal-seal and an output. The controller is programmed to detect at least one of a hot zone and a cool zone on the thermal-seal. The output device is communicably coupled to the output of the controller and indicates the results of the seal detection.

16 Claims, 4 Drawing Sheets

METHOD AND APPARATUS FOR MONITORING AND DETECTING DEFECTS IN PLASTIC PACKAGE SEALING

CROSS REFERENCES TO RELATED APPLICATIONS

The present application is a non-provisional application of co-pending provisional application No. 60/582,692, filed on Jun. 24, 2004, entitled "Method and Apparatus for Monitoring and Detecting Defects in Plastic Package Sealing," and is hereby incorporated by reference in its entirety for all purposes.

FIELD OF THE DISCLOSURE

The present disclosure is generally directed to method and apparatus for detecting defects in plastic sealing and, more particularly, a method and apparatus for detecting defects in plastic sealing using an infrared imaging system.

BACKGROUND OF THE DISCLOSURE

Thousands of different products are packaged in some kind of plastic container. The food industry uses them for such items as frozen pizza, frozen vegetables and fountain soda. The medical industry uses plastic bags for IV solutions and blood among others. In some cases a failed seal may affect the shelf life of the product or allow contaminants to enter. In another case, such as holding laundry detergent tablets, a failed seal is just a nuisance for the user. In any case, a failed seal ultimately reflects on the quality image of the supplier which may lead to a decline in future sales.

For some applications product is being sealed inside, while for others the product is the specialty plastic bag. Whether sealing in the final product or just making seals to create a bag, the process is similar. The product is indexed along the process line where it enters a heating press. The press is clamped on the areas to be sealed and then heat is applied until the plastic components are fused together. Heat is removed to start the cooling cycle before the press is released. The cycle repeats with the next part being indexed into position. Manufacturers run the cycle as quickly as possible to maximize production yield, but unfortunately the seal defects increase as the cycle speed is increased.

A thermal imaging system may function both as a tool to increase the cycle speed and also as an automatic fault detection system.

BRIEF DESCRIPTION OF THE DRAWINGS

Objects, features, and advantages of the present device will become apparent upon reading the following description in conjunction with the drawing figures, in which.

Figure 1:
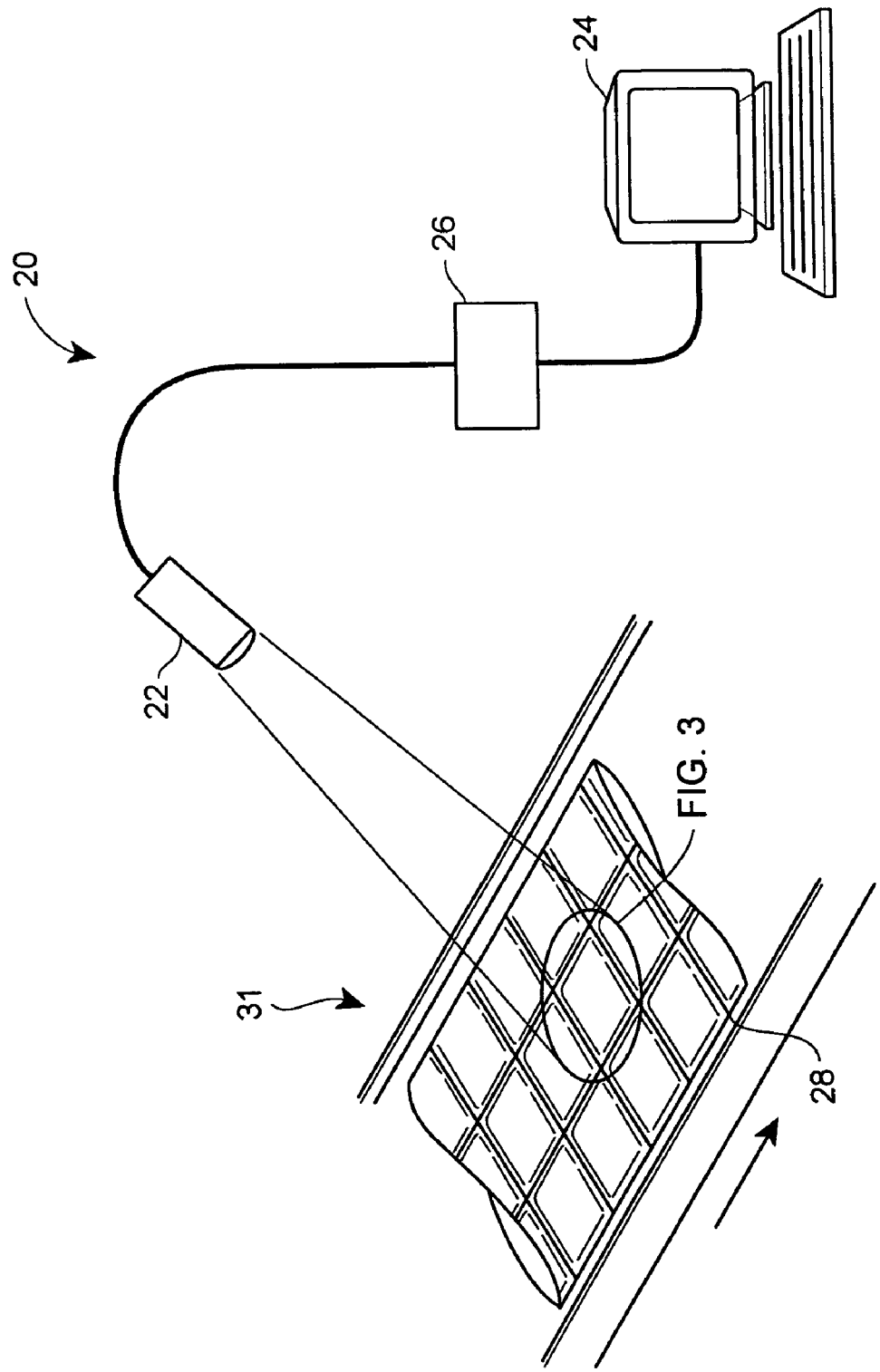
FIG. 1 is an isometric view of one example of an infrared imaging system used in detecting defects in plastic seals constructed according to one embodiment of the disclosure.

While the method and device described herein are susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the disclosure and the appended claims.

DETAILED DESCRIPTION OF THE DISCLOSURE

Figure 2:
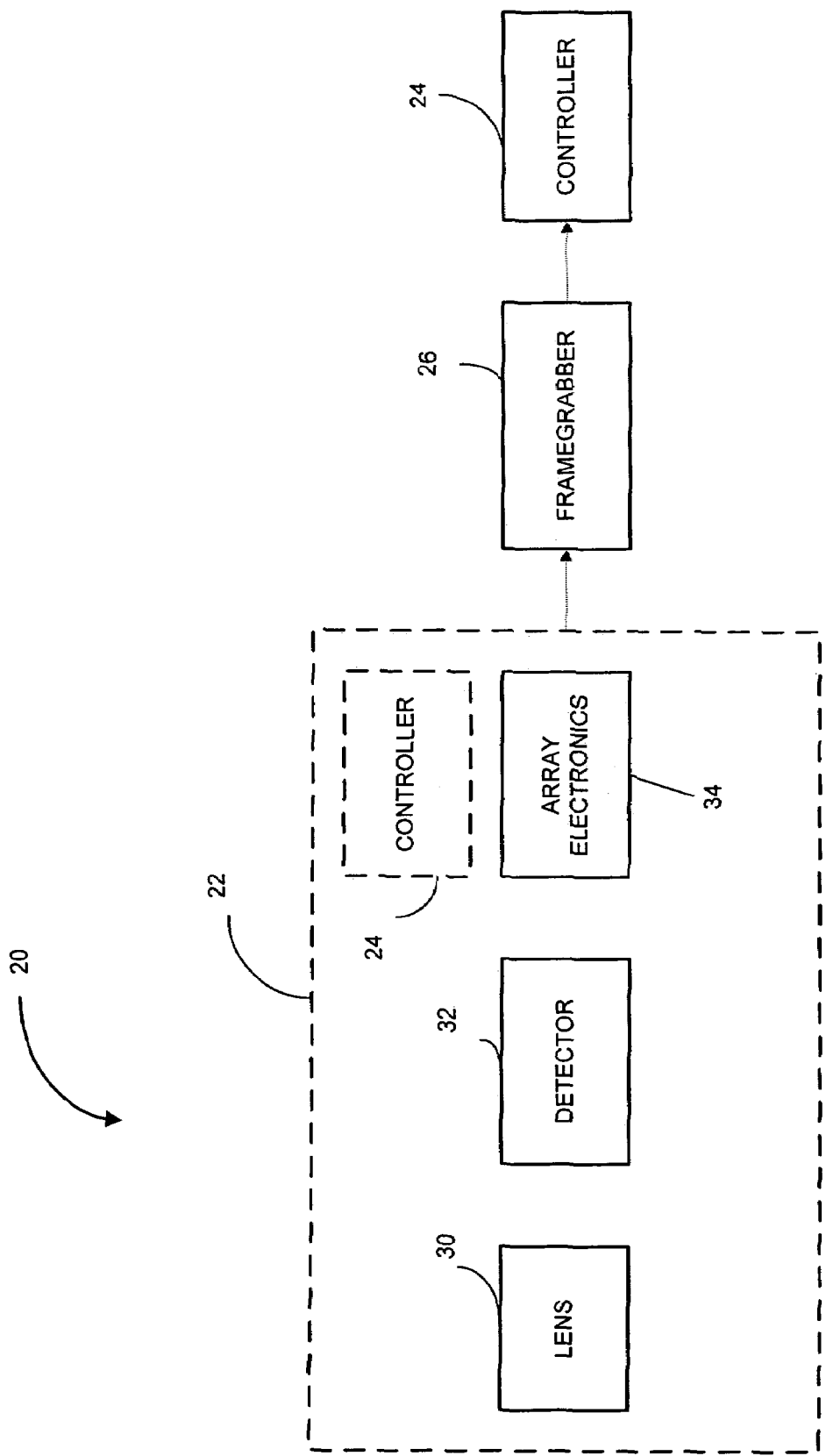
FIG. 2 is a block diagram of the infrared imaging system of FIG. 1.
Figure 4:
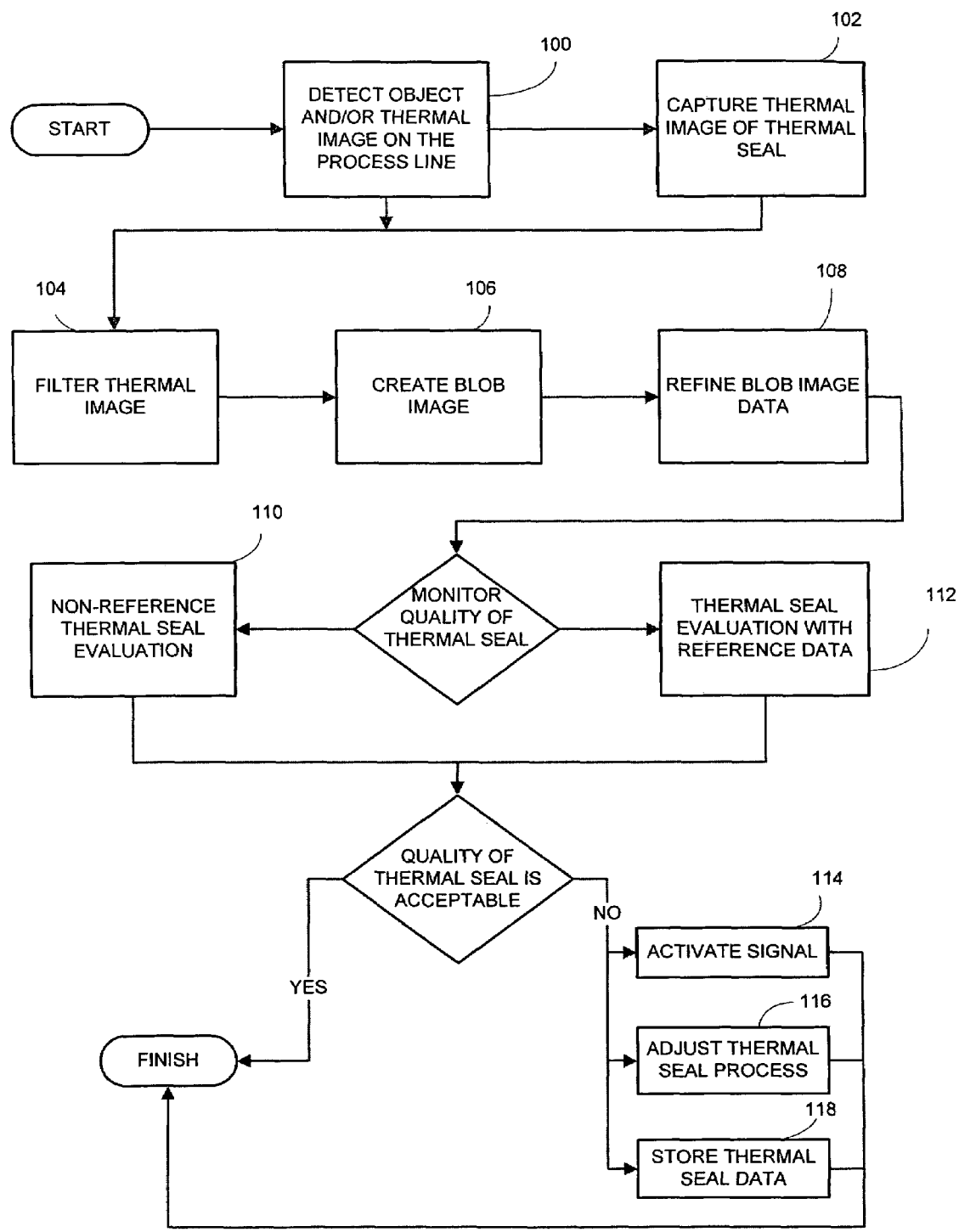
FIG. 4 is a flowchart of one exemplary operation of monitoring and detecting a defect in a thermal seal using the infrared imaging system of FIG. 1.

Referring now to the drawings and with specific reference to FIG. 1, an infrared imaging system constructed in accordance with the teachings of the disclosure is generally depicted by reference numeral 20. As shown therein, the imaging system 20 includes an infrared based thermal imaging camera 22 that is communicably coupled to a computing means 24 such as a common PC or controller that includes application software to implement the imaging system. The controller 24 may be disposed outside the camera 22, as seen in FIGS. 1 and 2, or may be disposed inside the camera (FIG. 2 shown in dashed lines). An interface 26 to couple the PC with the camera 22, such as a digital frame grabber 26, may be disposed between the controller 24 and the camera 22. As generally illustrated in FIG. 1 and in detail in FIG. 4, the thermal imager 22 captures a thermal image of one or more recently created seals 28. The thermal image is then processed and evaluated by the pre-programmed controller 24 to determine whether the seal 28 is of acceptable quality.

A variety of suppliers make thermal imagers that might be suitable for this application. One common type of infrared camera is based on microbolometer technology and has a typical spectral response range of 7 to 14 microns. Most of the packaging materials use thin plastics that have varying degrees of transmission in this region. The greater the transmission the more of the background the camera sees rather than the packaging material. Plastic has various regions which are substantially more opaque than others. There are many plastic formulations that will shift where the most opaque region is. To maximize the camera's sensitivity to the defects in the seals 28, the camera's spectral response should be tailored to the target material. There is a tradeoff in camera performance when the spectral range is reduced so it is best to make the spectral range as wide as possible. A good compromise for the microbolometer camera is a region of 7.5 to 8.2 microns. However, with other types of cameras a region centered near 3.4 microns may work as well.

As illustrated in FIG. 2, the camera 22 includes a lens 30 operatively connected to a detector or detector array 32. The camera 22 may also include a spectral filter to closely match the emission characteristics of the seal 28 or target material. The lens 30 optically compresses and guides the thermal image of the seal 28 onto the detector or detector array 32. The typical array 32 has a video format of 320×240 pixels yielding 76800 measurement point or pixels, but other array designs could use other formats, including but not limited to, 640×480 and 160×120. The array 30 is operatively connected to a plurality of array electronics 34 that convert the information in each piece of the array 32 to an electronic signal.

In one exemplary embodiment, the detector output is digitized with the results filling a block of memory in the controller 24 through the digital frame grabber 26. The frame grabber 26 may be used to digitize and/or store video information into a bitmap image, for example. Frame grabbers can be stand-alone units or may be a function built into video graphics boards in the camera 22.

The application software that is pre-programmed and stored in the controller 24 may have one or more components. One component of the application software is the part detection routine. An external signal could be used to signal each piece as it comes into view, but the software's auto detection logic may simplify the customer interface requirements. For example, as the part or target containing the seal 28 is moving in the field of view of the camera 22 there will be some pixels showing an increase in signal, due to the thermal activity on the target. In contrast, it is also true that some pixels will show a decrease in signal, due to the natural thermal decay that is occurring on the target. Such thermal decay is also present when the target is stationary. Therefore, sensing a decrease in signal may be an unreliable way of detecting motion.

Three variables, among others, may affect the reliability of this technique. One variable is inherent noise in the thermal imaging camera 22 which may be accounted for or covered by a temperature threshold delta adjustment. Another variable is slow moving targets which might not show enough signal change between frames. This variable may be accounted for by a setting that requires a minimum number of frames before the signal changes above the noise threshold. Finally, a false start or false trigger may be prevented or accounted for by an absolute minimum threshold temperature adjustment.

Another component of the application software is an image filtering routine. The image noise filtering relies on the concept that a hot object will cool at an exponential decay rate until it reaches thermal equilibrium with its surroundings. The routine collects data on every pixel, typically 76800 points, from every frame while the target is stationary. A best fit curve is computed for each individual pixel position using standard curve fitting techniques such as Gaussian reduction. Using such equations a clean thermal image is created along with a rate of change. It is even possible to extrapolate an image pattern for any point in time using the equations. The rate of change is important for detecting certain types of sealing faults. It is important to note that while an exponential equation is best for extrapolating images beyond the observation period a simple linear equation is usually sufficient for the fault detection logic.

Another component of the application software is commonly referred to in the vision industry as blob analysis. The blob result comes from a common function in vision systems that convert the image so that it contains only black pixels and white pixels, and thereby removes any shades of gray from the image. This is accomplished by comparing each raw pixel value against some threshold. If the value is greater than the threshold then the corresponding blob pixel is made white, otherwise it-is set to black. The resulting blob pattern is sometimes easier to work with in locating parts and in doing dimensional analysis on the part.

In other words, a binary pattern is generated from the thermal image obtained from the thermal imager 22. If a pixel is above some threshold it is set to 1 otherwise it is set to 0. The blob pattern is defined by the pixels which the seal defect analysis operates on. In a number of situations it is possible to generate a complete thermal outline of the seal area, including the defective areas, because all these areas are heated. Accordingly, no reference image or data is required because the seal analysis can be completed by comparing or analyzing various portions of the seal area and the seal 28 relative to each other.

In other situations it will be necessary to rely on the blob data from a known, good reference image. In a real process the image location will shift somewhat from one part to the next. The benefit of not using a reference is that there is no need for software realignment of the test image against the reference image. The drawback to not using a reference image is that there are less failure detection criteria to choose from. Of course the user may choose to use both reference and non-reference based schemes together to either reduce false defect signals or missed faults.

Another component of the application software provides refinement of the blob pattern to make the blob pattern useful in thermal fault detection schemes. In particular, data near edges of the seal 28 may indicate temperatures substantially lower than they should. This is mainly due to the actual seal boundary not aligning with the camera's pixel boundary, but may also be due to thermal leakage into adjacent cooler areas and other factors. Accordingly, the software may use a blob thinning or blob fattening routine to affect boundaries of the seal 28.

One thinning scheme is based on looking at eight surrounding pixels of any particular pixel. If the surrounding pixels are all ones then a one is written a 1 to the new blob, otherwise is written a 0. Other trimming or thinning schemes may prove useful under certain circumstances. For example, if the seal 28 is just a horizontal bar you may only want to look at the pixels above and below the seal 28.

One fattening scheme, for aligning the blob pattern with a reference blob, for example, includes looking at the eight surrounding pixels of a pixel and writing a one if any of the surrounding pixels is a one, or writing a 0 if they all are zero. The image is then incrementally shifted up, down, left, and right a reasonable number of pixels and correlated against the reference image. The adjusted alignment is then assumed to be the position that yields the highest correlation.

Another blob refinement scheme is to allow the user to manually edit the reference blob adding or subtracting to the image, but many other blobbing schemes, additional to the ones disclosed herein, may be used.

Another component of the application software provides the detection of faults or failures in the seal 28. The faults may be detected by using a reference or a non-reference detection scheme.

There are two schemes for detecting faults without comparing to a reference. The two schemes each look at the value of the thermal data only at the locations where the blob pattern has a 1. The first scheme looks at the absolute temperature and if any pixel is below some adjustable threshold a fault is indicated. The second scheme looks at the rate of change of the pixels and, again, if any pixel is below some adjustable threshold a fault is indicated. The rate of change scheme best detects faults originating from extra material occurring in the seal area. The extra material may be from a fold in the plastic or other contaminants. The material still reaches the same absolute temperature in the press but the larger mass slows the cooling rate and, hence, is detected.

There are several fault detection schemes that may be implemented when comparing against a reference. One technique is calculating the correlation between the test image and the reference image. The sensitivity of this technique is improved by using only thermal data corresponding to the fat blob results. Other techniques may include the standard deviation or the maximum deviation between the images, but many other fault detection schemes, additional to the ones disclosed herein, may be used.

The results of each of the detection schemes may be combined logically in various ways to produce a single pass fail indication. The system may provide one or more methods of notifying the user of the pass/fail result. Two common outputs may be a relay contact and TCP/IP based communications. The results of the detection schemes may also be utilized in many other ways, with various types of output devices. For example, an output of the controller 24 may be communicably coupled to a monitor or display for viewing the seal 28.

Figure 3:
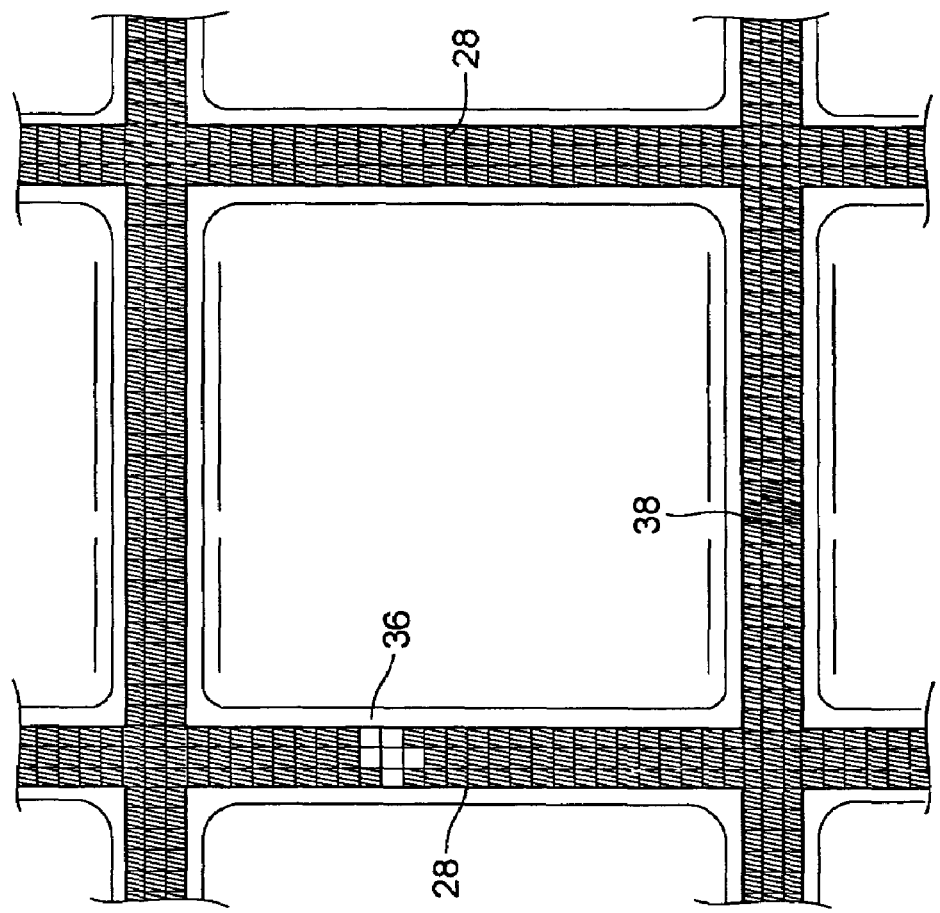
FIG. 3 is an example of a partial thermal image of a plurality of seals as obtained from the infrared imaging system of FIG. 1.

In operation, the imaging system 20 may be used to detect a fault in the seal 28, and may be used to measure the quality of the seal 28. The seal 28 may come in many shapes and forms, and may be used in a great variety of applications and environments, but for clarity and brevity the seal 28 used herein is a simple seal constructed by the joining of two plastic layers, as is illustrated in FIG. 3.

The two layers of plastic, one disposed on top of the other, may be disposed on a conveyer system 31 (FIG. 1), or the like, during the seal creation and seal inspection process. As the seal 28 comes into the view of the thermal imaging camera 22, the imaging system 20 may obtain one or more thermal images of the seal 28. The thermal image may be used for indexing or locating the seal 28 (block 100), but may be used for later analysis. Alternatively, a separate thermal image for analysis of the seal 28 may be obtained at block 102. Once the thermal image has been obtained, the imaging system 20 may begin a filtering routine to enhance the image quality (block 104). At block 106 the thermal image may be converted into a blob image or pattern, which may then be refined at block 108. Using a reference or non-reference methodology, at blocks 112 and 110, respectively, the imaging system 20 may inspect the seal 28 to determine if a fault or other undesirable quality is present in the seal 28, or if the seal 28 meets approval. For example, as seen in FIG. 2, the image resulting from the seal 28 may show a cool spot or zone 36 indicating that the seal 28 may be too thin or that a hole has been created in the seal 28 during the sealing process. In contrast, the image resulting from the seal 28 may show a hot spot or zone 38 indicating that the seal 28 may be too thick or that an extra layer of plastic or debris has been made part of the seal 28. The information resulting from the inspection of the seal 28 may then be utilized in several manners. For example, if the quality of the seal 28 is unacceptable, the information may be stored on the PC or controller 24 or other electronic device communicably coupled to the imaging system 20 at block 118, the information may be used to active a signal or alarm, such as "good" or "bad" at block 114, and/or may be used to adjust or alter the manufacturing process at block 116. If the quality of the seal 28 is acceptable, however, the inspection of other seals may continue.

Although certain embodiments of an imaging system 20 have been described herein in accordance with the teachings of the present disclosure, the scope of coverage of this patent is not limited thereto. On the contrary, this patent covers all embodiments of the teachings of the disclosure that fairly fall within the scope of permissible equivalents.

What is claimed is:

1. An apparatus for monitoring and detecting thermal sealing defects, comprising:
    a thermal imager mounted along a process line, the process line transporting an object having at least one recently created thermal-seal thereon;
    a controller having an input and an output, the input being communicably coupled to the thermal imager for receiving thermal image data of the thermal-seal, the controller being programmed to create a blob pattern including only two colors of pixels from the thermal image data, and to detect at least one of a hot zone and a cool zone on the thermal-seal; and
    a output device communicably coupled to the output of the controller, wherein the output device indicates the results of the seal detection.

2. The apparatus of claim 1, wherein the output device is a display depicting the seal detection.

3. The apparatus of claim 1, wherein the output device is an alarm activated upon the detection of at least one of the hot zone and the cool zone.

4. The apparatus of claim 1, further including an indexing device, external to the controller, wherein the indexing device is mounted along the process line and indexes the object relative to the thermal imager.

5. The apparatus of claim 1, wherein the controller is programmed to thin the blob pattern created from the thermal image of the seal.

6. The apparatus of claim 1, wherein the controller is programmed to fatten the blob pattern created from the thermal image of the seal.

7. The apparatus of claim 1, further including a reference image for comparison to the thermal image data.

8. The apparatus of claim 1, wherein the controller is programmed to index the object relative to the thermal imager by utilizing the blob pattern created from the thermal image of the object.

9. The apparatus of claim 1, further including a spectral filter to closely match the emission characteristics of the object.

10. A fault detection system for a thermal seal created by fusing a plurality of materials together on a process line, comprising:
    a thermal imaging camera; and
    a controller operatively coupled to the thermal imaging camera and an output device;
    the controller being programmed to store application software relating to the fault detection system,
    the controller being programmed to process an image of a thermal seal received from the thermal image camera and create a blob pattern including only two colors of pixels from the thermal image data, and
    the controller being programmed to detect a fault in the thermal seal using the processed image by detecting at least one of a hot zone and a cool zone on the thermal seal.

11. The fault detection system of claim 10, wherein the thermal imager includes a spectral filter to closely match the emission characteristics of a target material.

12. The fault detection system of claim 10, wherein the controller is programmed to separate pixels of the thermal image into at least a first group and a second group.

13. The fault detection system of claim 10, wherein the controller is programmed to compare the thermal image to a reference image.

14. A method of monitoring and detecting thermal sealing defects, comprising:
    placing a thermal imager along a process line, the process line transporting an object having at least one recently created thermal-seal thereon;
    capturing a thermal image of the thermal seal;
    creating a blob pattern from the thermal image;
    converting the thermal image to a plurality of pixels of only two colors in accordance with the blob pattern;
    detecting at least one of a hot zone and a cool zone on the thermal seal using a controller; and
    indicating the results of seal detection using an output device coupled to the controller.

15. The method of claim 14, further comprising thinning the blob pattern created from the thermal image.

16. The method of claim 14, further comprising fattening the blob pattern created from the thermal image.

* * * * *